United States Patent
Sarvazyan et al.

(10) Patent No.: US 7,931,588 B2
(45) Date of Patent: Apr. 26, 2011

(54) SYSTEM FOR ASSESSMENT OF COLONOSCOPE MANIPULATION

(75) Inventors: Armen P. Sarvazyan, Lambertville, NJ (US); Sergey Tsyuryupa, Westampton, PA (US); Vladimir Egorov, Princeton, NJ (US); Brendan Corbin, Tewksbury, MA (US); Louis Y. Korman, Rockville, MD (US)

(73) Assignee: Artann Laboratories, West Trenton, NJ (US)

( * ) Notice: Subject to any disclaimer, the term of this patent is extended or adjusted under 35 U.S.C. 154(b) by 107 days.

(21) Appl. No.: 12/558,837

(22) Filed: Sep. 14, 2009

(65) Prior Publication Data

US 2011/0065989 A1    Mar. 17, 2011

(51) Int. Cl.
    *A61B 1/00* (2006.01)
(52) U.S. Cl. ......................................... 600/131; 600/117
(58) Field of Classification Search .................. 600/101, 600/131, 117, 118, 587
    See application file for complete search history.

(56) References Cited

U.S. PATENT DOCUMENTS

| | | | |
|---|---|---|---|
| 4,411,257 A | 10/1983 | Machida | |
| 4,846,155 A * | 7/1989 | Kimura | 600/109 |
| 5,496,260 A | 3/1996 | Krauter et al. | |
| 6,100,920 A * | 8/2000 | Miller et al. | 348/68 |
| 6,168,569 B1 * | 1/2001 | McEwen et al. | 600/557 |
| 6,315,736 B1 * | 11/2001 | Tsutsumi et al. | 600/500 |
| 6,817,973 B2 * | 11/2004 | Merril et al. | 600/118 |
| 6,926,531 B2 | 8/2005 | Wallaker | |
| 6,981,945 B1 * | 1/2006 | Sarvazyan et al. | 600/131 |
| 7,037,258 B2 * | 5/2006 | Chatenever et al. | 600/109 |
| 7,248,281 B2 * | 7/2007 | Abe | 348/65 |
| 7,300,398 B2 | 11/2007 | Chefd'hotel et al. | |
| 7,403,811 B2 | 7/2008 | Sathyanarayana | |
| 7,627,189 B2 * | 12/2009 | Donomae et al. | 382/254 |
| 7,805,178 B1 * | 9/2010 | Gat | 600/407 |
| 2001/0016804 A1 * | 8/2001 | Cunningham et al. | 703/7 |
| 2004/0206365 A1 * | 10/2004 | Knowlton | 128/898 |
| 2006/0055544 A1 * | 3/2006 | Morguelan | 340/573.1 |
| 2006/0161045 A1 * | 7/2006 | Merril et al. | 600/117 |
| 2008/0146875 A1 * | 6/2008 | Noguchi et al. | 600/117 |
| 2009/0055019 A1 * | 2/2009 | Stiehl et al. | 700/249 |
| 2009/0292226 A1 * | 11/2009 | Feng et al. | 600/595 |
| 2010/0228100 A1 * | 9/2010 | Vining | 600/300 |

* cited by examiner

*Primary Examiner* — John P Leubecker
(74) *Attorney, Agent, or Firm* — Boris Leschinsky

(57) ABSTRACT

A comprehensive system for objective assessment of colonoscope manipulation includes a handgrip for collecting and transmitting colonoscope handling data including force and motion data; a patient pain monitor for collecting and transmitting data on the level of patient's pain and discomfort; and digital processing means for extracting useful features such as colonoscope tip advancement speed from colonoscope-provided video images. All data is wirelessly transmitted to an electronic unit for processing and displaying on a monitor. A colonoscopy procedure is properly conducted when certain shaft advancement causes appropriate tip advancement, all without an increased level of patient's pain. The system of the invention is aimed at providing objective assessment data allowing for safer and less painful colonoscopies.

3 Claims, 3 Drawing Sheets

SYSTEM FOR ASSESSMENT OF COLONOSCOPE MANIPULATION

REFERENCE TO GOVERNMENT-SPONSORED RESEARCH

This invention was made with the U.S. government support under SBIR grant No. R44 DK068936-02 entitled "Colonoscope Force Monitor" and awarded by the National Institute of Health, National Institute of Diabetes and Digestive and Kidney Diseases. The government has certain rights in this invention.

BACKGROUND OF THE INVENTION

The present invention relates generally to devices useful for improving the operator's skills in manipulating steerable catheters and scopes. In particular, the invention describes a device for assessing colonoscope manipulation and maneuvering. The invention allows simultaneous measuring and display of colonoscope insertion forces and torques, linear and rotational accelerations of the colonoscope shaft, real time images of the colon, and patient's pain level throughout the procedure.

In many cases, it has been desirable to examine internal organs, passages and the like of the human body for purposes of diagnosis, biopsy, and therapeutic interventions. One method of examining the internal organs of the patient without major surgery is to insert a remote sensing device such as an endoscope into the body through a natural body orifice such as a colon or a specially-prepared surgical opening.

Although the preferred application of the invention is for use with a colonoscope, other devices can also be coupled to the device disclosed herein. Therefore, the word "colonoscope" is used throughout this description to broadly include various types of direct vision and fiber optic endoscopes, fiberscopes, arthoscopes, laparoscopes, and other types or steerable and deflectable catheters and tubes designed to be inserted into tight openings and curved passages.

The use of steerable scopes for internal examination is not limited to medicine. Remote sensing devices can be used to examine the interior of otherwise inaccessible mechanical structures without opening them, such as aircraft wings, the walls of buildings, and the enclosed areas of any structure. In these cases, an internal examination without putting a major opening in the structure can help to determine the reason for mechanical failure or the level of corrosion levels.

The preferred area of interest for the device of the present invention is in medicine, and more particularly in colonoscopy. Colonoscopy is the preferred method to screen for colorectal cancer, a disease that affects 150 thousand patients per year in the US. Several million screening, diagnostic and therapeutic colonoscopies are performed each year in the U.S. hospitals and ambulatory surgery centers. Colonoscopy requires a physician to inspect the colonic mucosal surface by applying force to a colonoscope and advancing this flexible tube through a series of stationary and movable colonic loops.

When using a colonoscope, a common problem is to be able to maneuver the inspection end of the scope and position it in proximity to the area of interest. This maneuvering is performed by a trained operator who uses a combination of visual assessment of images obtained by colonoscope and tactile coordination to advance the shaft of the colonoscope through the twists and turns of the colon. The operator subjectively senses the resistance to maneuvers by the "feel" of the instrument and anticipates the amount of force necessary to advance the device forward. The application of force to the colon and its anatomic structures can be painful for the patient. Particularly undesirable is the frequent occurrence of excessive contact pressure on an internal tissue, which can result in perforation. Sedation with analgesia is frequently required to make the procedure comfortable for the patient. Preliminary studies suggest that there is significant variation in forces applied by different operators and that these forces can be excessive. Operator training programs are designed to reduce the variation in technique, however training metrics remain subjective and the characterization of effective, less forceful insertion methods is not yet available. The need therefore exists to provide a device allowing an effective, low-cost method to define the best practices and to implement these practices as part of training, ongoing education and quality assurance.

There is an extensive array of surgical instruments, catheters and endoscopes that can be introduced and guided into and through both solid and hollow organ systems such as gastrointestinal tract, blood vessels and heart, urologic and gynecologic systems. These devices are designed to perform a variety of functions such as illumination, introduction of radiographic contrast materials and other fluids, surgical therapies, dilatation, etc.

Examples of such guiding or steering techniques and systems for catheters are found in U.S. Pat. No. 4,983,165 to Loiterman entitled "Guidance System For Vascular Catheter Or The Like," U.S. Pat. No. 4,776,844 to Ueda entitled "Medical Tube," U.S. Pat. No. 4,934,340 to Ebling et al. entitled "Device For Guiding Medical Catheters and Scopes," U.S. Pat. No. 4,930,521 to Metzget et al. entitled "Variable Stiffness Esophageal Catheter," U.S. Pat. No. 3,470 to Barchilon entitled "Dirigible Catheter," U.S. Pat. No. 3,605, 725 to Bentov entitled "Controlled Motion Devices," and the PCT patent application Ser. No. WO88/00810 of Tenerz et al. entitled "Guide For Mechanical Guiding Of A Catheter In Connection With Cardio And Vessel Examination." These catheters, however, fail to give the operator sufficient control of the distal end of the catheter and make it difficult to manipulate the distal end for specific isolation of particular sections of the body vessel or cavity.

Other steerable catheters or systems have been made to try to give the physician control of the use of the catheter during surgical procedures. Fluids and various mechanisms are employed for controlling the direction of movement of the distal end of the catheter. Examples of these attempts are found in the PCT patent application Ser. No. WO91/11213 of Lundquist et al. entitled "Catheter Steering Mechanism," European Patent Application No. 370,158 of Martin entitled "Catheter For Prolonged Access," and U.S. Pat. No. 4,737, 142 to Heckele entitled "Instrument for Examination and Treatment of Bodily Passages." These devices, however, still fail to provide sufficient control and manipulation of the catheter needed for use with the surgical tools and fluids required for a procedure such as colonoscopy.

A handheld force measuring device to be used with the colonoscope tube is disclosed in U.S. Pat. No. 6,981,945 issued to Sarvazyan, et al. entitled "Colonoscope Handgrip with Force and Torque Monitor" incorporated herein in its entirety by reference. It describes a handgrip attachment for a colonoscope shaft capable of measuring and presenting to the operator of radial and longitudinal forces applied by the operator during the manipulation of the colonoscope. The handgrip includes a set of sensors such as strain gages positioned on all sides of a rectangular bar to measure the forces between the handgrip and the shaft of the colonoscope. The measurements are then transmitted to an electronic unit for data processing and then further to a display system such as a personal computer.

U.S. Pat. No. 5,881,321 to Kivolowitz, Mar. 9, 1999, discloses a system for using absolute position of a hand-held camera by use of inertial sensors incorporated into the structure of the camera to detect the movement of the camera along three orthogonal axes, as well as angular rotation around the three axes. U.S. Pat. No. 6,097,423 to Mattsson-Boze, et al., Aug. 1, 2000, discloses an endoscope and camera with which a display observed through the optics in the endoscope is rotated to a desired orientation using an accelerometer. The accelerometer generates a signal indicative of the local vertical and is used in the particular embodiment to rotate a CCD image sensor aligned with the optical axis of the endoscope so as to maintain a desired orientation of a display of the image on a monitor. U.S. Pat. No. 7,211,042 to Chatenever, et al., May 1, 2007 describes the endoscope video camera system with an inertial sensor to sense rotations of the received image about the optical axis of the endoscope and the sensor's output signals are used to rotate either the image or the image sensor. In case of rotation of the image sensor as the rotation sensor can be used a gyroscope or a pair of accelerometers. These inventions are related to a re-orientation of an image as viewed on a display screen to present the image in a preferred relationship to the viewer's reference frame. Proposed solutions however do not allow using visual data for evaluation of endoscope motion.

A more advanced version of that device is shown in our co-pending U.S. patent application Ser. No. 12/558,737 filed on Sep. 14, 2009 and entitled "A handgrip for Assessment of Colonoscope Manipulation" incorporated herein in its entirety by reference. This device includes force and torque sensors as well as linear and rotational acceleration sensors. This combination of sensors allows detecting not only the input forces and torques applied to the colonoscope shaft but also the resulting movement of the shaft in or out of the patient. Obstacles or obstructions to the advancement of the instrument are detected when sufficient force is not accompanied by expected advancement of the shaft.

Still, characterization of the movement of the shaft is only one part of the comprehensive characterization of the colonoscopy procedure. The second part is the patient and the level of discomfort or pain caused by manipulation of the shaft. The third and final part of this characterization is the final result of colonoscopy, namely the image of the specific parts of the colon provided by the scope.

The need exists for a comprehensive system that can tie together these three parts of the colonoscopy procedure, namely the manipulation of the colono scope shaft, level of patient's pain and discomfort as well as the image of the colon.

SUMMARY OF THE INVENTION

Accordingly, it is an object of the present invention to overcome these and other drawbacks of the prior art by providing a novel comprehensive system for objective assessment of colonoscopy based on a characterization of colonoscope motion, characterization of patient's pain, and characterization of tip advancement derived from colonoscope-provided images.

The system of the invention is based on three categories of data obtained in real time during the colonoscopy procedure:
information pertaining to the input forces applied to the colonoscope shaft, and the motion of the shaft resulting from these forces;
information about the level of pain or discomfort felt by the patient, and
information derived from the video images obtained by the colono scope during the procedure.

All three categories of data are transmitted to the signal acquisition and data collection unit and processed to objectively and quantitatively characterize the colonoscope manipulations. Obtained data may be used for record keeping and for training purposes.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
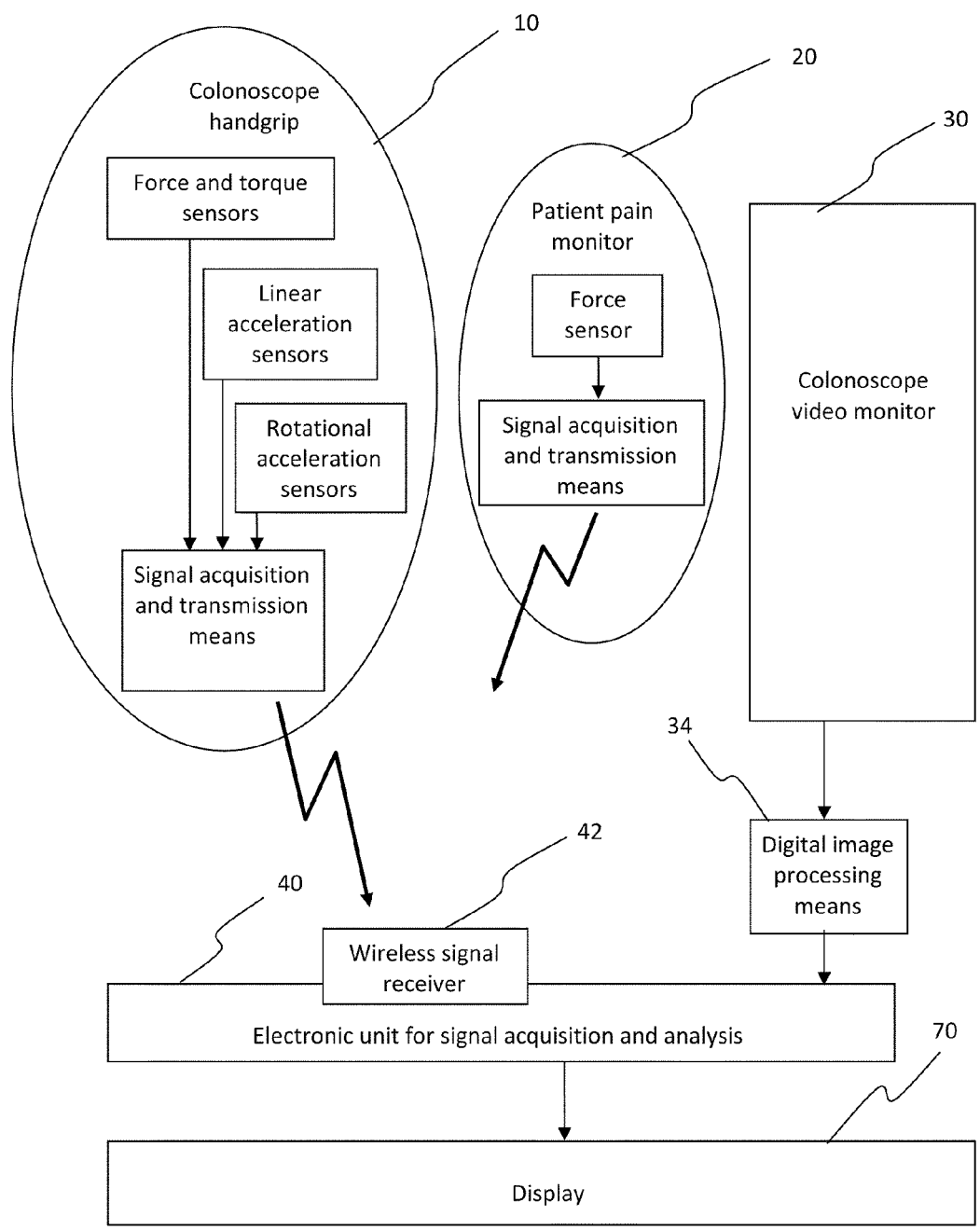
FIG. 1 is a block-diagram of the system of the present invention.

Major components of the system of the invention are shown in FIG. 1. They include means for characterizing colonoscope handling such as a colonoscope handgrip 10 equipped with sensors characterizing colonoscope manipulations by the medical practitioner; a patient pain monitor 20; preferably a colonoscope video monitor tower 30; an electronic unit 40 for signal acquisition and analysis; and an optional display 70.

Data transfers from the handgrip and pain monitor to the electronic unit 40 are preferably made by wireless connection to avoid having cables attached to the handgrip and the pain monitor. Electronic unit 40 is adapted data processing, analysis and presentation of results on display 70. Units 40 and 70 can be combined together or can be based on a desktop or laptop computer.

A variety of sensors may be located within the handgrip allowing capturing the push or pull forces, torque as well as handgrip linear and rotational accelerations as it is shown in FIG. 1. It is envisioned that in other embodiments of the invention the manipulation data may include extended set of sensors to measure also handgrip orientation angles (elevation, rotation angles), handgrip speed (linear and rotational) and handgrip position in real time. The digital image processing means 34 provides real time image features extraction for evaluation of manipulation technique of the operator. Also, image processing means 34 provides real time image information for estimation of the colonoscope tip motion.

The extracted set of features may include image sharpness, brightness and contrast distribution. All these features and their changes in time can be used for assessment of the colonoscope tip motion.

The colonoscope tip motion might be subdivided into linear and rotational movements being calculated from a sequence of acquired digital images with the use of known motion tracking algorithm or their combinations from an algorithmic set including active contour technique, traditional gradient descent method, Bayesian statistical technique, Kalman filter, centroid and correlation measurements for target detection, alpha-beta filter, multi-target tracking technique, snake driven by annealing methods, Markov Chain Monte Carlo approach, sequential Bayesian algorithm (S. Acton, "Biomedical Image Analysis: Tracking." Morgan & Claypool Publishers, 2006, pp. 1-144; A. Cavallaro, F. Porikli, C. S. Regazzoni, "Video Tracking in Complex Scenes for Surveillance Applications", Hindawi Publishing Corporation, 2009, pp 1-168.). Analysis of the colonoscope image changes in time allows determining linear and rotational speed of a tip of the colonoscope.

Figure 2:
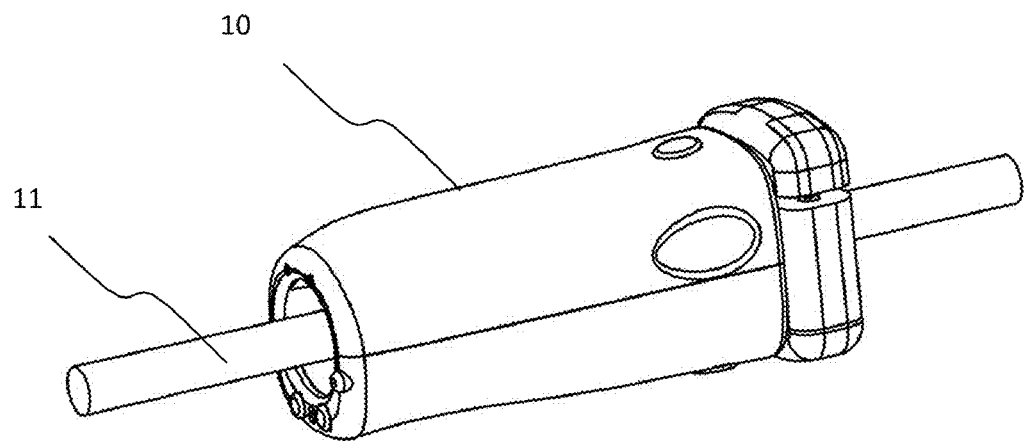
FIG. 2 is general view of the colonoscope handgrip equipped with manipulation assessment sensors.

A colonoscope handgrip 10 serving as a means for characterizing colonoscope handling is generally shown on FIG. 2. It is placed over a shaft 11 of the colonoscope and is shaped to fit in a human hand. The details of various design approaches of the handgrip can be found in our U.S. Pat. No. 6,981,945 and in our co-pending U.S. patent application Ser. No. 12/558,737. Both documents describe a colonoscope handgrip equipped with an internal sleeve adapted to releasably grip onto a colonoscope shaft, and an external sleeve adapted to be manipulated by a medical practitioner. An engagement means are provided to connect the internal sleeve with the external sleeve. A variety of sensors are incorporated between the internal sleeve and external sleeve allowing characterizing the forces applied to the shaft and its resulting movement.

Figure 3:
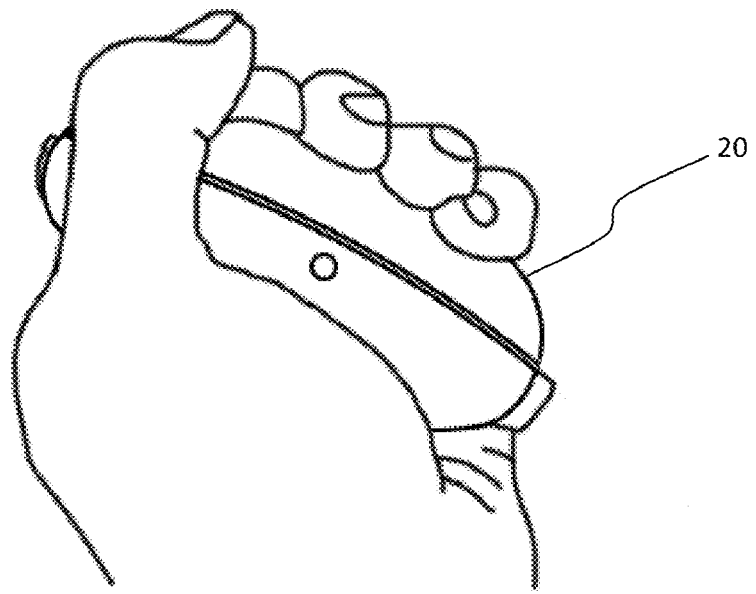
FIG. 3 is a general view of the patient pain monitor in use by a patient.

A patient pain monitor 20 is generally shown in FIG. 3. It is placed on a patient's hand and retained there with a strap. The detailed description of this device is found in our co-pending U.S. patent application Ser. No. 12/558,775 filed Sep. 14, 2009 and entitled "Pain Monitor for a Patient Undergoing a Medical Procedure". This document is incorporated herein in its entirety by reference.

Briefly, the pain monitor 20 includes a housing having two halves with a force sensor placed therebetween. The patient is instructed to squeeze the housing proportionally to the level of pain and discomfort that he or she experiences. The force of squeezing the housing is measured by an internal force sensor. Internal battery-powered data processor converts the force sensor data into a signal representing the level of pain by the patient. The signal is then wirelessly transmitted to the electronic unit 40 for further processing and recording.

Linear and rotational advancement of the tip of the colonoscope can be extracted by analyzing a series of progressive images provided by the colonoscope tip. The image processing means is adapted to recognize anatomical features and elements of the colon. Advancement of the tip changes the position of these elements on the image. Such changes are recognized by the image processing means and translated into the speed or advancement or rotation by the tip of the colonoscope.

Combining the parameters characterizing the advancement of the tip of the colonoscope with parameters characterizing the handling and advancement of the shaft of the colonoscope outside the patient as well as the patient's pain level allows a complete characterization of the colonoscopy procedure.

When force is applied to the shaft, it is anticipated that certain shaft advancement would correspond with the advancement of the colonoscope tip. Lack of tip advancement coupled with a possible increase in pain while applying push force onto the colonoscope shaft cumulatively indicates an obstacle or obstruction or possible improper handling of the shaft by a medical practitioner. On the other hand, the presence of shaft advancement, tip advancement and lack of pain indicate proper progression of colonoscopy evaluation.

Figure 4:
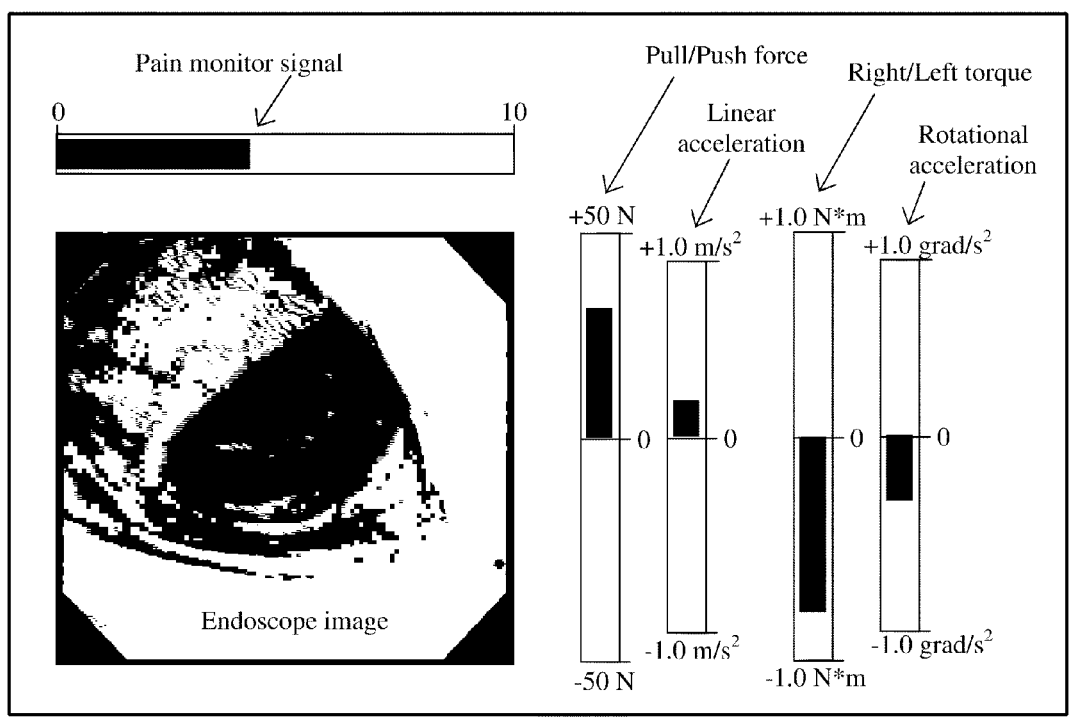
FIG. 4 shows user interface of the system of the current invention.

FIG. 4 shows an example of the user interface screen of the unit 70. Plurality of data generated by the handgrip 10, pain monitor 20 and the colonoscope video monitor is shown all in one place on the same screen. Viewing all the data from the shaft manipulation, patient's pain level and the image from the scope allows physician to conveniently monitor the progression of colonoscopy. All data can be recorded for record keeping and for later post-processing and analysis.

Although the invention herein has been described with respect to particular embodiments, it is understood that these embodiments are merely illustrative of the principles and applications of the present invention. For example, it is envisioned to have a device allowing viewing only the colonoscope movement and patient pain data but not the image from the scope. Such device may be useful as a stand-alone adjunct to the standard colonoscope image tower. It is therefore to be understood that numerous modifications may be made to the illustrative embodiments and that other arrangements may be devised without departing from the spirit and scope of the present invention as defined by the appended claims.

What is claimed is:

1. A system for assessment of colonoscope manipulation comprising:
    a means for characterizing colonoscope shaft handling, said means adapted to collect and transmit colonoscope shaft handling data including forces applied to said colonoscope shaft and its movement resulting therefrom,
    a colonoscope video monitor adapted for receiving, processing and displaying a colonoscope-provided video image,
    a patient pain monitor adapted to collect and transmit data characterizing patient's pain and discomfort,
    an electronic unit adapted to receive and process colonoscope shaft handling data and patient pain monitor data,
    a digital image processing means adapted to extract image features from said video image and transmit them to said electronic unit, said digital image processing means is adapted to determine linear and rotational speed of a tip of said colonoscope from a series of progressive images supplied by said video monitor.

2. The system as in claim 1, wherein said image features include at least one feature selected from a group of features consisting of sharpness, brightness and contrast distribution.

3. The system as in claim 1, wherein said electronic unit is equipped with a display presenting received data in real time.

\* \* \* \* \*